United States Patent
Lennhoff et al.

(10) Patent No.: US 7,682,782 B2
(45) Date of Patent: Mar. 23, 2010

(54) SYSTEM, METHOD, AND PRODUCT FOR MULTIPLE WAVELENGTH DETECTION USING SINGLE SOURCE EXCITATION

(75) Inventors: Akim F. Lennhoff, Cambridge, MA (US); Nathan K. Weiner, Upton, MA (US)

(73) Assignee: Affymetrix, Inc., Santa Clara, CA (US)

( * ) Notice: Subject to any disclaimer, the term of this patent is extended or adjusted under 35 U.S.C. 154(b) by 1179 days.

(21) Appl. No.: 11/260,617

(22) Filed: Oct. 27, 2005

(65) Prior Publication Data

US 2006/0094048 A1  May 4, 2006

Related U.S. Application Data

(60) Provisional application No. 60/623,390, filed on Oct. 29, 2004.

(51) Int. Cl.
*C12Q 1/00* (2006.01)
(52) U.S. Cl. .......................................................... 435/4
(58) Field of Classification Search ........................ None
See application file for complete search history.

(56) References Cited

U.S. PATENT DOCUMENTS

| | | | |
|---|---|---|---|
| 5,171,534 A | 12/1992 | Smith et al. | |
| 5,578,832 A | 11/1996 | Trulson et al. | |
| 5,672,880 A | 9/1997 | Kain | |
| 6,274,323 B1 | 8/2001 | Bruchez et al. | |
| 6,306,610 B1 | 10/2001 | Bawendi et al. | |
| 6,326,144 B1 | 12/2001 | Bawendi et al. | |
| 6,496,309 B1 | 12/2002 | Bliton et al. | |
| 6,500,622 B2 * | 12/2002 | Bruchez et al. ................ 435/6 |
| 6,617,590 B2 | 9/2003 | Nishioka et al. | |
| 6,734,420 B2 | 5/2004 | Empedocles et al. | |
| 6,759,235 B2 | 7/2004 | Empedocles et al. | |
| 6,768,122 B2 | 7/2004 | Dong et al. | |
| 6,774,361 B2 | 8/2004 | Bawendi et al. | |
| 6,794,658 B2 | 9/2004 | MacAulay et al. | |
| 7,198,939 B2 * | 4/2007 | Dorsel et al. ............. 435/283.1 |
| 2001/0055764 A1 | 12/2001 | Empedocles et al. | |
| 2002/0009728 A1 | 1/2002 | Bittner et al. | |
| 2003/0034486 A1 | 2/2003 | Korgel | |
| 2003/0059635 A1 | 3/2003 | Naasani | |
| 2003/0099940 A1 | 5/2003 | Empedocles et al. | |
| 2003/0162215 A1 | 8/2003 | Iwao et al. | |
| 2003/0175773 A1 | 9/2003 | Chee et al. | |
| 2004/0009341 A1 | 1/2004 | Naasani | |
| 2004/0012676 A1 | 1/2004 | Weiner et al. | |
| 2004/0014202 A1 | 1/2004 | King et al. | |
| 2004/0022684 A1 | 2/2004 | Heinze et al. | |
| 2004/0061071 A1 * | 4/2004 | Dorsel ..................... 250/458.1 |
| 2005/0260741 A1 | 11/2005 | Albertson et al. | |

OTHER PUBLICATIONS

EPO Search Report. Application No. 05400035.1-2204. Apr. 18, 2006.

* cited by examiner

*Primary Examiner*—Ann Y Lam
(74) *Attorney, Agent, or Firm*—Thomas J. Siepmann

(57) ABSTRACT

An embodiment of a method for adjusting system gain of a biological probe array scanner for a plurality of fluorophore species is described that comprises setting an excitation beam comprising an excitation wavelength at a first power level that elicits an optimal signal to noise ratio response from a first fluorophore species; scanning a biological probe array with the excitation beam; setting the excitation beam comprising the excitation wavelength at a second power level different than the first power level that elicits the optimal signal to noise ratio response from a second fluorophore species; and scanning the biological probe array with the excitation beam.

24 Claims, 8 Drawing Sheets

SYSTEM, METHOD, AND PRODUCT FOR MULTIPLE WAVELENGTH DETECTION USING SINGLE SOURCE EXCITATION

RELATED APPLICATIONS

The present application claims priority from U.S. Provisional Patent Application Ser. No. 60/623,390, titled "System, Method and Product for Multiple Wavelength Detection Using Single Source Excitation", filed Oct. 29, 2004, which is hereby incorporated by reference herein in its entirety for all purposes.

BACKGROUND

1. Field of the Invention

The present invention relates to systems and methods for examining biological material. In particular, the invention relates to improved optical readers or scanners for detection of multiple wavelength emissions using a single source of excitation light, where each emitted wavelength is associated with a label coupled with a hybridized probe target pair on a biological probe array.

2. Related Art

Synthesized nucleic acid probe arrays, such as Affymetrix GeneChip® probe arrays, and spotted probe arrays, have been used to generate unprecedented amounts of information about biological systems. For example, the GeneChip® Human Genome U133 Plus 2.0 Array available from Affymetrix, Inc. of Santa Clara, Calif., is comprised of one microarray containing 1,300,000 oligonucleotide features covering more than 47,000 transcripts and variants that include 38,500 well characterized human genes. Analysis of expression data from such microarrays may lead to the development of new drugs and new diagnostic tools.

SUMMARY OF THE INVENTION

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials produced by the Affymetrix® 417™ or 427™ Arrayer. Other illustrative implementations are referred to in relation to data from Affymetrix® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

An embodiment of a method for adjusting system gain of a biological probe array scanner for a plurality of fluorophore species is described that comprises setting an excitation beam comprising an excitation wavelength at a first power level that elicits an optimal signal to noise ratio response from a first fluorophore species; scanning a biological probe array with the excitation beam; setting the excitation beam comprising the excitation wavelength at a second power level different than the first power level that elicits the optimal signal to noise ratio response from a second fluorophore species; and scanning the biological probe array with the excitation beam.

Also some implementations of the described embodiment may include setting the excitation beam comprising the excitation wavelength at a third power level different than the first and second power levels that elicits the optimal signal to noise ratio response from a third fluorophore species; scanning the biological probe array with the excitation beam; setting the excitation beam comprising the excitation wavelength at a fourth power level different than the first, second, and third power levels that elicits the optimal signal to noise ratio response from a fourth fluorophore species; and scanning the biological probe array with the excitation beam.

A system for scanning a plurality of fluorophore species is also described that comprises an instrument control application stored for execution in system memory of a computer, wherein the application performs the method comprising; setting an excitation beam comprising an excitation wavelength at a first power level that elicits an optimal signal to noise ratio response from a first fluorophore species; scanning a biological probe array with the excitation beam; setting the excitation beam comprising the excitation wavelength at a second power level different than the first power level that elicits the optimal signal to noise ratio response from a second fluorophore species; and scanning the biological probe array with the excitation beam.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 160 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION a) General

Figure 1:
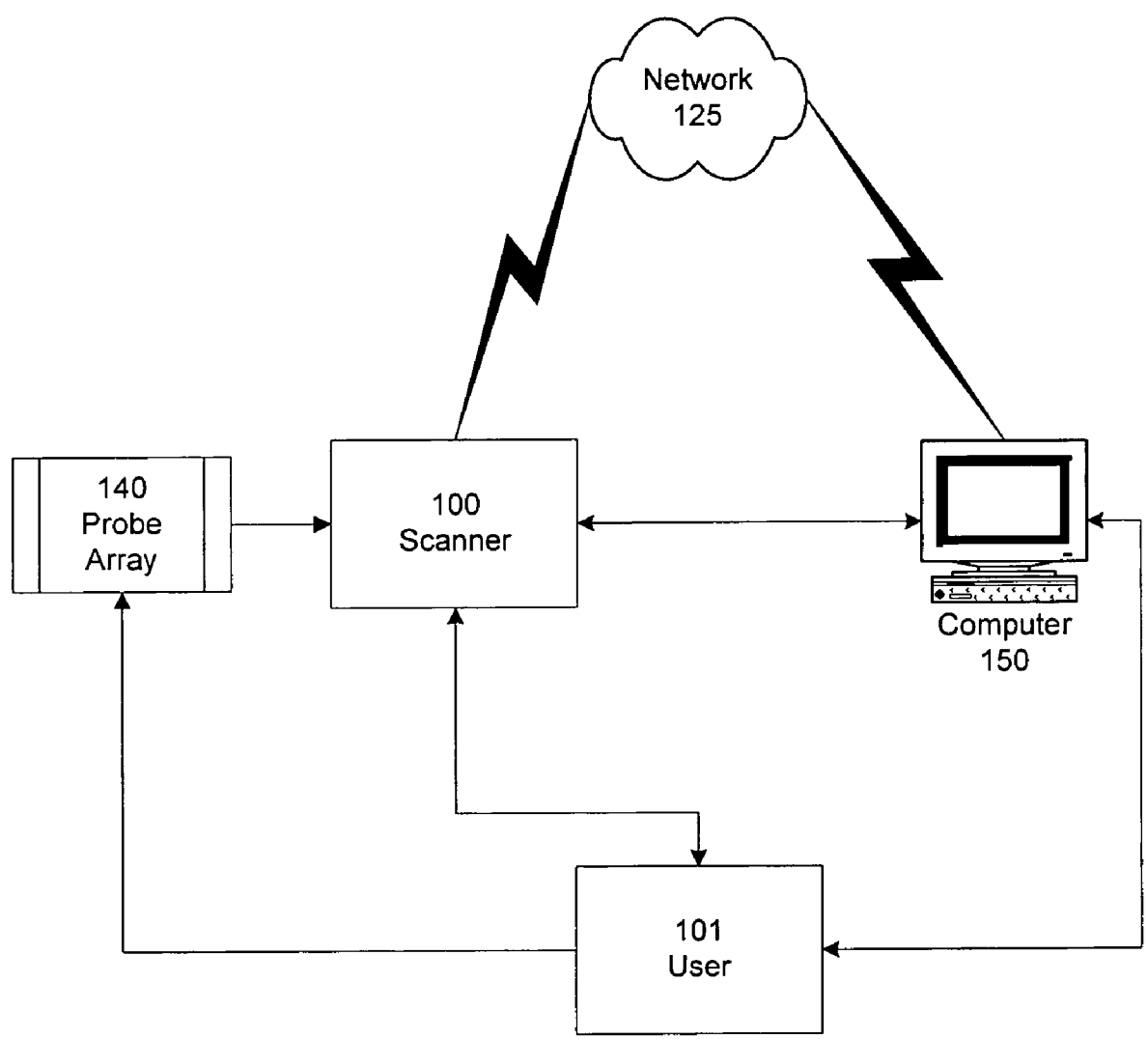
FIG. 1 is a functional block diagram of one embodiment of a scanner instrument enabled to scan a probe array and computer system for image acquisition and analysis.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841; WO 00/58516; U.S. Pat. Nos. 5,143,854; 5,242,974; 5,252,743; 5,324,633; 5,384,261; 5,405,783; 5,424,186; 5,451,683; 5,482,867; 5,491,074; 5,527,681; 5,550,215; 5,571,639; 5,578,832; 5,593,839; 5,599,695; 5,624,711; 5,631,734; 5,795,716; 5,831,070; 5,837,832; 5,856,101; 5,858,659; 5,936,324; 5,968,740; 5,974,164; 5,981,185; 5,981,956; 6,025,601; 6,033,860; 6,040,193; 6,090,555; 6,136,269; 6,269,846; and 6,428,752; in PCT Applications Nos. PCT/US99/00730 (International Publication No. WO 99/36760); and PCT/US01/04285 (International Publication No. WO 01/58593); which are all incorporated herein by reference in their entirety for all purposes.

Patents that describe synthesis techniques in specific embodiments include U.S. Pat. Nos. 5,412,087; 6,147,205; 6,262,216; 6,310,189; 5,889,165; and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992; 6,013,449; 6,020,135; 6,033,860; 6,040,138; 6,177,248; and 6,309,822. Genotyping and uses therefore are shown in U.S. Ser. Nos. 10/442,021; 10/013,598 (U.S. Patent Application Publication 20030036069); and U.S. Pat. Nos. 5,856,092; 6,300,063; 5,858,659; 6,284,460; 6,361,947; 6,368,799; and 6,333,179. Other uses are embodied in U.S. Pat. Nos. 5,871,928; 5,902,723; 6,045,996; 5,541,061; and 6,197,506.

The present invention also contemplates sample preparation methods in certain preferred embodiments. Prior to or concurrent with genotyping, the genomic sample may be amplified by a variety of mechanisms, some of which may employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202; 4,683,195; 4,800,159;

4,965,188; and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909; 5,861, 245) and nucleic acid based sequence amplification (NABSA). (See, U.S. Pat. Nos. 5,409,818; 5,554,517; and 6,063,603, each of which is incorporated herein by reference). Other amplification methods that may be used are described in, U.S. Pat. Nos. 5,242,794; 5,494,810; 4,988,617; and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. N. 6,361,947, 6,391,592 and U.S. Ser. Nos. 09/916,135; 09/920,491 (U.S. Patent application Publication 20030096235); Ser. No. 09/910,292 (U.S. Patent Application Publication 20030082543); and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y, 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928; 5,874,219; 6,045,996; 6,386,749; and 6,391,623 each of which are incorporated herein by reference.

The present invention also contemplates signal detection of hybridization between ligands in certain preferred embodiments. For example, methods and apparatus for signal detection and processing of intensity data are disclosed in, U.S. Pat. Nos. 5,143,854; 5,547,839; 5,578,832; 5,631,734; 5,800,992; 5,834,758; 5,856,092; 5,902,723; 5,936,324; 5,981,956; 6,025,601; 6,090,555; 6,141,096; 6,171,793; 6,185,030; 6,201,639; 6,207,960; 6,218,803; 6,225,625; 6,252,236; 6,335,824; 6,403,320; 6,407,858; 6,472,671; 6,490,533; 6,650,411; and 6,643,015, in U.S. patent application Ser. Nos. 10/389,194; 60/493,495; and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,733,729; 5,593,839; 5,795,716; 5,733,729; 5,974,164; 6,066,454; 6,090,555; 6,185,561; 6,188,783; 6,223,127; 6,228,593; 6,229,911; 6,242,180; 6,308,170; 6,361,937; 6,420,108; 6,484,183; 6,505,125; 6,510,391; 6,532,462; 6,546,340; and 6,687,692.

Additionally, the present invention may have preferred embodiments that include methods for providing genetic information over networks such as the Internet as shown in U.S. Ser. Nos. 10/197,621; 10/063,559 (U.S. Publication Number 20020183936); Ser. Nos. 10/065,856; 10/065,868; 10/328,818; 10/328,872; 10/423,403; and 60/482,389.

b) Definitions

The term "admixture" refers to the phenomenon of gene flow between populations resulting from migration. Admixture can create linkage disequilibrium (LD).

The term "allele" as used herein is any one of a number of alternative forms a given locus (position) on a chromosome. An allele may be used to indicate one form of a polymorphism, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a bioploymer is a "biomonomer".

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "effective amount" as used herein refers to an amount sufficient to induce a desired result.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "hybridization" as used herein refers to the process in which two single-stranded polynucleotides bind noncovalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C are suitable for allele-specific probe hybridizations or conditions of 100 mM MES, 1 M [Na+], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), LNAs, as described in Koshkin et al. Tetrahedron 54:3607-3630, 1998, and U.S. Pat. No. 6,268, 490, aptamers, and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" or sometimes referred to as "allelic association" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., Nat. Rev. Gen. 3:299-309, 2002.

The term "mendelian inheritance" as used herein refers to The term "lod score" or "LOD" is the log of the odds ratio of the probability of the data occurring under the specific hypothesis relative to the null hypothesis. LOD=log [probability assuming linkage/probability assuming no linkage].

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (MRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "MRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the MRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, Principles of Biochemistry, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

c) Embodiments of the Present Invention

Embodiments of a scanning system are described herein that are enabled to detect multiple wavelengths of light emitted from labels associated with hybridized probe/target pairs, where the emitted light is responsive to a wavelength or range of wavelengths provided by a single source. In particular, embodiments are described that are enabled to accurately image features of a probe array that may include feature sizes in a range of 24 µm to 5 µm or smaller in a dimension (such as the side of a square, side of a rectangle, or diameter of a spot). It may be advantageous in certain embodiments to employ assays that include a plurality of different labels that uniquely distinguish a particular aspect that is associated with each label. For example, those of ordinary skill in the related art will appreciate that what are referred to as "Genotyping" assays benefit from the use of multiple labels. Genotyping assays may include what are referred to as sequencing, or the determination of genotype (i.e. determination of allele composition, polymorphisms, etc.) types of assays, where the assay depends heavily on the correct identification of particular nucleic acids in a sequence. In the present example, the assay may include a unique label associated with each type of nucleic acid in a DNA sequence, such as the A, C, G, or T, where each labels emits a unique wavelength responsive to an excitation beam. The multiple label assay allows for the unambiguous determination of the nucleic acid composition of a sequence.

Probe Array 240: An illustrative example of probe array 240 is provided in FIGS. 1, 2, and 3. Descriptions of probe arrays are provided above with respect to "Nucleic Acid Probe arrays" and other related disclosure. In various implementations of probe array 240 may be disposed in a cartridge or housing such as, for example, the GeneChip® probe array available from Affymetrix, Inc. of Santa Clara Calif. Examples of probe arrays and associated cartridges or housings may be found in U.S. Pat. Nos. 5,945,334, 6,287,850, 6,399,365, 6,551,817, each of which is also hereby incorporated by reference herein in its entirety for all purposes. In addition, some embodiments of probe array 240 may be associated with pegs or posts some examples of which may be found in U.S. patent Ser. No. 10/826,577, titled "Immersion Array Plates for Interchangeable Microtiter Well Plates", filed Apr. 16, 2004, which is hereby incorporated by reference herein in its entirety for all purposes.

Scanner 100: Labeled targets hybridized to probe arrays may be detected using various devices, sometimes referred to as scanners, as described above with respect to methods and apparatus for signal detection. An illustrative device is shown in FIG. 1 as scanner 100, and in greater detail in FIG. 2 that for instance includes scanner optics and detectors 200. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 µm, 1.5 µm, 1.0 µm, or sub-micron pixel size. Two examples where the signal may be incorporated into data are data files in the form *.dat or *.tif as generated respectively by Affymetrix® Microarray Suite (described in U.S. patent application Ser. No. 10/219,882, which is hereby incorporated by reference herein in its entirety for all purposes) or Affymetrix® GeneChip® Operating Software (described in U.S. patent application Ser. No. 10/764,663, which is hereby incorporated by reference herein in its entirety for all purposes ) based on images scanned from GeneChip® arrays, and Affymetrix® Jaguar™ software (described in U.S. patent application Ser. No. 09/682,071, which is hereby incorporated by reference herein in its entirety for all purposes) based on images scanned from spotted arrays. Examples of scanner systems that may be implemented with embodiments of the present invention include U.S. patent application Ser. Nos. 10/389,194; and 10/913,102, both of which are incorporated by reference above; and U.S. patent application Ser. No. 10/846,261, titled "System, Method, and Product for Providing A Wavelength-Tunable Excitation Beam", filed May 13, 2004, which is hereby incorporated by reference herein in its entirety for all purposes.

Computer 150: An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input devices 240, and display/output devices 245. Display/Output Devices 245 may include display devices that provides visual information, this information typically may be logically and/or physically organized as an array of pixels. A Graphical user interface (GUI) controller may also be included that may comprise any of a variety of known or future software programs for providing graphical input and output interfaces such as for instance GUI's 246. For example, GUI's 246 may provide one or more graphical representations to a user, such as user 101, and also be enabled to process user inputs via GUI's 246 using means of selection or input known to those of ordinary skill in the related art.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor such as an Itanium® or Pentium® processor made by Intel Corporation, a SPARC® processor made by Sun Microsystems, an Athalon™ or Opteron™ processor made by AMD corporation, or it may be one of other processors that are or will become available. Processor 255 executes operating system 260, which may be, for example, a Windows®-type operating system (such as Windows NT® 4.0 with SP6a, or Windows XP) from the Microsoft Corporation; a Unix® or Linux-type operating system available from many vendors or what is referred to as an open source; another or a future operating system; or some combination thereof. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk drive, or a diskette drive. Such types of memory storage devices 281 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

Figure 2:
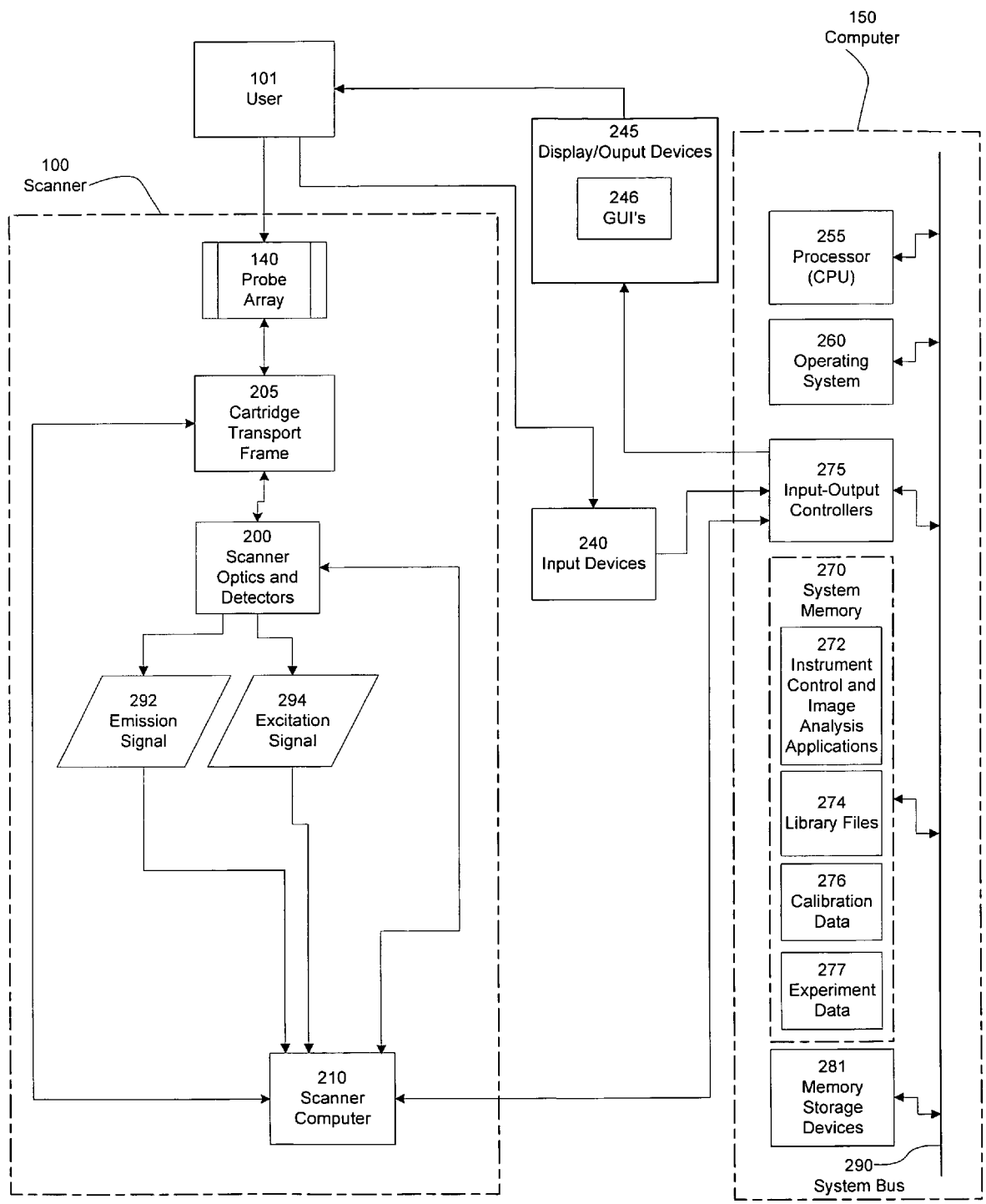
FIG. 2 is a functional block diagram of one embodiment of the scanner-computer system of FIG. 1, including a cartridge transport frame, scanner optics and detectors, and a scanner computer.

As will be evident to those skilled in the relevant art, instrument control and image processing applications 272, if implemented in software, may be loaded into and executed from system memory 270 and/or memory storage device 281. All or portions of applications 272 may also reside in a read-only memory or similar device of memory storage device 281, such devices not requiring that applications 272 first be loaded through input-output controllers 275. It will be understood by those skilled in the relevant art that applications 272, or portions of it, may be loaded by processor 255 in a known manner into system memory 270, or cache memory (not shown), or both, as advantageous for execution. Also illustrated in FIG. 2 are library files 274, calibration data 276, and experiment data 277 stored in system memory 270. For example, calibration data 276 could include one or more values or other types of calibration data related to the calibration of scanner 100 or other instrument. Additionally, experiment data 277 could include data related to one or more experiments or assays such as excitation wavelength ranges, emission wavelength ranges, extinction coefficients and/or associated excitation power level values, or other values associated with one or more fluorescent labels.

Network 125 may include one or more of the many various types of networks well known to those of ordinary skill in the art. For example, network 125 may include what is commonly referred to as a TCP/IP network, or other type of network that may include the internet, or intranet architectures.

Instrument control and image processing applications 272: Instrument control and image processing applications 272 may be any of a variety of known or future image processing applications. Examples of applications 272 include Affymetrix® Microarray Suite, Affymetrix® GeneChip® Operating Software (hereafter referred to as GCOS), and Affymetrix® Jaguar™ software, noted above. Applications 272 may be loaded into system memory 270 and/or memory storage device 281 through one of input devices 240.

Embodiments of applications 272 include executable code being stored in system memory 270 of an implementation of computer 150. Applications 272 may provide a single interface for both the client workstation and one or more servers such as, for instance, GeneChip® Operating Software Server (GCOS Server). Applications 272 could additionally provide the single user interface for one or more other workstations and/or one or more instruments. In the presently described implementation, the single interface may communicate with and control one or more elements of the one or more servers, one or more workstations, and the one or more instruments. In the described implementation the client workstation could be located locally or remotely to the one or more servers and/or one or more other workstations, and/or one or more instruments. The single interface may, in the present implementation, include an interactive graphical user interface that allows a user to make selections based upon information presented in the GUI. For example, applications 272 may provide an interactive GUI that allows a user to select from a variety of options including data selection, experiment parameters, calibration values, probe array information. Applications 272 may also provide a graphical representation of raw or processed image data where the processed image data may also include annotation information superimposed upon the image such as, for instance, base calls, features of the probe array, or other useful annotation information. Further examples of providing annotation information on image data are provided in U.S. Provisional Patent Application Ser. No. 60/493,950, titled "System, Method, and Product for Displaying Annotation Information Associated with Microarray Image Data", filed Aug. 8, 2003, which is hereby incorporated by reference herein in its entirety for all purposes.

In alternative implementations, applications 272 may be executed on a server, or on one or more other computer platforms connected directly or indirectly (e.g., via another network, including the Internet or an Intranet) to network 125.

Embodiments of applications 272 also include instrument control features. The instrument control features may include the control of one or more elements of one or more instruments that could, for instance, include elements of a fluidics station, what may be referred to as an autoloader, and scanner 100. The instrument control features may also be capable of receiving information from the one more instruments that could include experiment or instrument status, process steps, or other relevant information. The instrument control features could, for example, be under the control of or an element of the single interface. In the present example, a user may input desired control commands and/or receive the instrument control information via one of GUI's 246. Additional examples of instrument control via a GUI or other interface is provided in U.S. Provisional Patent Application Ser. No. 60/483,812, titled "System, Method and Computer Software for Instrument Control, Data Acquisition and Analysis", filed Jun. 30, 2003, which is hereby incorporated by reference herein in its entirety for all purposes.

In some embodiments, image data is operated upon by applications 272 to generate intermediate results. Examples of intermediate results include so-called cell intensity files (*.cel) and chip files (*.chp) generated by Affymetrix® GeneChip® Operating Software or Affymetrix® Microarray Suite (as described, for example, in U.S. patent application Ser. Nos. 10/219,882, and 10/764,663, both of which are hereby incorporated herein by reference in their entireties for all purposes) and spot files (*.spt) generated by Affymetrix® Jaguar™ software (as described, for example, in PCT Application PCT/US 01/26390 and in U.S. patent applications, Ser. Nos. 09/681,819, 09/682,071, 09/682,074, and 09/682,076, all of which are hereby incorporated by reference herein in their entireties for all purposes). For convenience, the term "file" often is used herein to refer to data generated or used by applications 272 and executable counterparts of other applications, but any of a variety of alternative techniques known in the relevant art for storing, conveying, and/or manipulating data may be employed.

For example, applications 272 receives image data derived from a GeneChip® probe array and generates a cell intensity file. This file contains, for each probe scanned by scanner 100, a single value representative of the intensities of pixels measured by scanner 100 for that probe. Thus, this value is a measure of the abundance of tagged mRNA's present in the target that hybridized to the corresponding probe. Many such mRNA's may be present in each probe, as a probe on a GeneChip® probe array may include, for example, millions of oligonucleotides designed to detect the mRNA's. As noted, another file illustratively assumed to be generated by applications 272 is a chip file. In the present example, in which applications 272 include Affymetrix® GeneChip® Operating Software, the chip file is derived from analysis of the cell file combined in some cases with information derived from lab data and/or library files 274 that specify details regarding the sequences and locations of probes and controls. The resulting data stored in the chip file includes degrees of hybridization, absolute and/or differential (over two or more experiments) expression, genotype comparisons, detection of polymorphisms and mutations, and other analytical results.

In another example, in which applications 272 includes Affymetrix® Jaguar™ software operating on image data from a spotted probe array, the resulting spot file includes the intensities of labeled targets that hybridized to probes in the array. Further details regarding cell files, chip files, and spot files are provided in U.S. patent application Ser. Nos. 09/682,074 incorporated by reference above, as well as Ser. No. 10/126,468; and 09/682,098; which are hereby incorporated by reference herein in their entireties for all purposes. As will be appreciated by those skilled in the relevant art, the preceding and following descriptions of files generated by applications 272 are exemplary only, and the data described, and other data, may be processed, combined, arranged, and/or presented in many other ways.

User 101 and/or automated data input devices or programs (not shown) may provide data related to the design or conduct of experiments. As one further non-limiting example related to the processing of an Affymetrix® GeneChip® probe array, the user may specify an Affymetrix catalogue or custom chip type (e.g., Human Genome U133 plus 2.0 chip) either by selecting from a predetermined list presented by GCOS or by scanning a bar code, Radio Frequency Identification (RFID), or other means of electronic identification related to a chip to read its type. GCOS may associate the chip type with various scanning parameters stored in data tables including the area of the chip that is to be scanned, the location of chrome borders on the chip used for auto-focusing, the wavelength or intensity/power of excitation light to be used in reading the chip, and so on. As noted, applications 285 may apply some of this data in the generation of intermediate results. For example, information about the dyes may be incorporated into determinations of relative expression.

Those of ordinary skill in the related art will appreciate that one or more operations of applications 272 may be performed by software or firmware associated with various instruments. For example, scanner 100 could include a computer that may include a firmware component that performs or controls one or more operations associated with scanner 100, such as for instance scanner computer 210 and scanner firmware 472.

Figure 4:
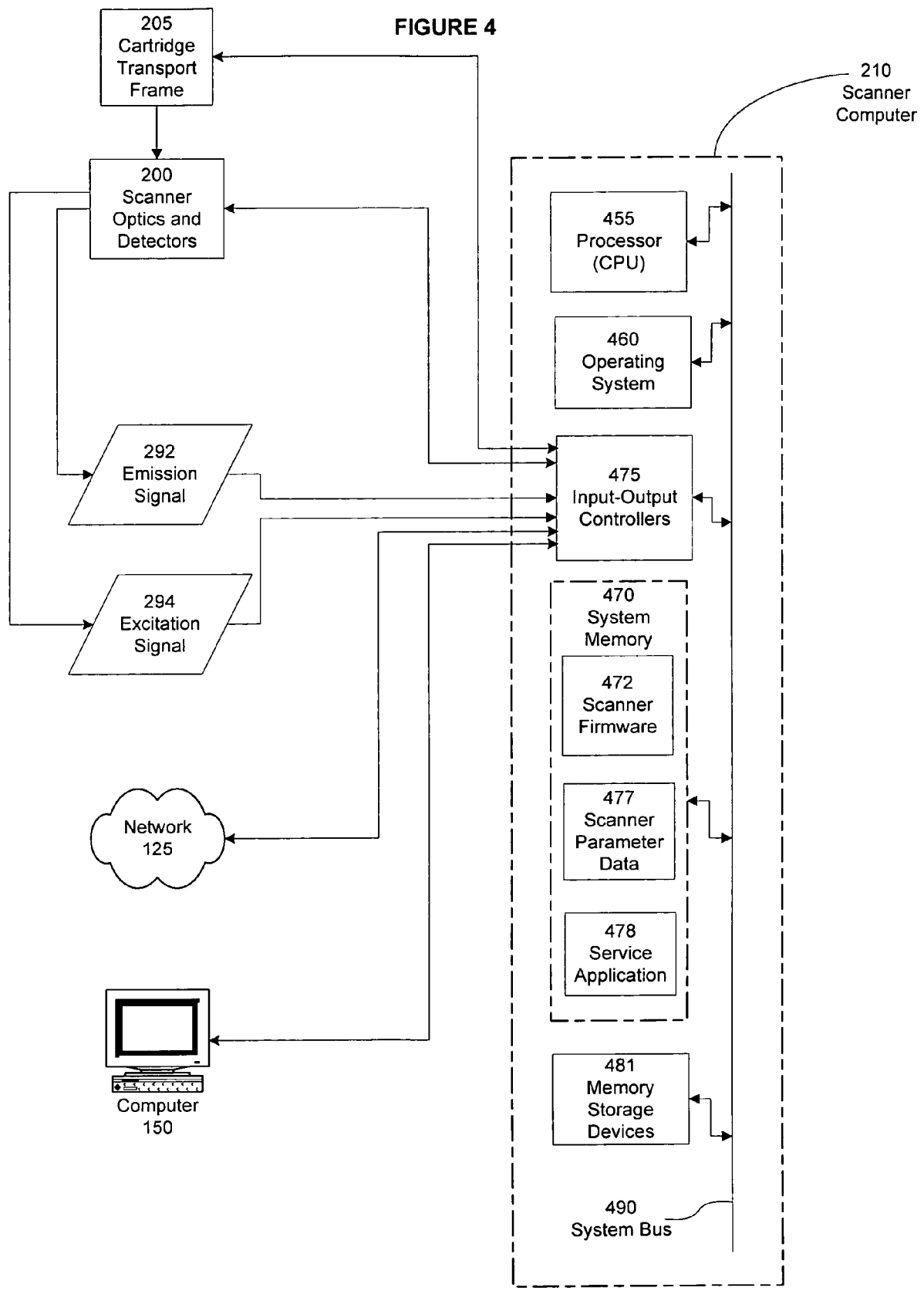
FIG. 4 is a functional block diagram of one embodiment of the scanner computer of FIG. 3, including a sensor board.

Scanner Computer 210: As illustrated in FIG. 4, scanner computer 210 may include elements such as sensor board 453, processor 455, operating system 460, input-output controllers 475, system memory 470, memory storage devices 481, and system bus 490 that may, in some implementations, have the same characteristics of corresponding elements in computer 150. Other elements of scanner computer 210 may include scanner firmware 472, scanner parameter data 477, and service application 478 that will each be described in detail below.

Scanner firmware 472 may, in many implementations, be enabled to control all functions of scanner 100 based, at least in part, upon data stored locally in scanner parameter data 477 or remotely in one or more data files from one or more remote sources. For example, the remote data source could include computer 150 that includes library files 274, calibration data 276, and experiment data 277 stored in system memory 270. In the present example, the flow of data to scanner computer 210 may be managed by instrument control and image analysis applications 272 that may be responsive to data requests from firmware 472.

A possible advantage of including scanner computer 210 in a particular implementation is that scanner 100 may be network based and/or otherwise arranged so that a user computer, such as computer 150, is not required. Input-output controllers 475 may include what is commonly referred to by those of ordinary skill in the related art as a TCP/IP network connection. The term "TCP/IP" generally refers to a set of protocols that enable the connection of a number of different networks into a network of networks (i.e. the Internet). Scanner computer 210 may use the network connection to connect to one or more computers, such as computer 150, in place of a traditional configuration that includes a "hardwire" connection between a scanner instrument and a single computer. For example, the network connection of input-output controllers 475 may allow for scanner 100 and one more computers to be located remotely from one another. Additionally, a plurality of users, each with their own computer, may utilize scanner 100 independently. In some implementations it is desirable that only a single computer is allowed to connect to scanner 100 at a time. Alternatively, a single computer may interact with a plurality of scanners. In the present example, all calibration and instrument specific information may be stored in one or more locations in scanner computer 210 that may be made available to the one or more computers as they interface with scanner computer 210.

The network based implementation of scanner 100 described above may include methods that enable scanner 100 to operate unimpaired during averse situations that, for instance, may include network disconnects, heavy network loading, electrical interference with the network connection, or other types of adverse event. In some implementations, scanner 100 may require a periodic signal from computer 150 to indicate that the connection is intact. If scanner 100 does not receive that signal within an expected period of time, scanner 100 may operate on the assumption that the network connection has been lost and start storing data that would have been transmitted. When the network connection has been reacquired to scanner 100, all collected data and related information may be transferred to computer 150 that would have normally been transferred if the network connection remained intact. For example, during the occurrence of an adverse situation scanner 100 may lose the network connection to computer 150. The methods enable scanner 100 to operate normally including the acquisition of image data and other operations without interruption. Scanner 100 may store the acquired image data of at least one complete scanned image in memory storage devices 481 to insure that the data is not lost.

In some embodiments, scanner computer 210 may also enable scanner 100 to be configured as a standalone instrument that does not depend upon a controlling workstation. Scanner computer 210 may acquire and store image data as well as function as a data server to multiple clients for efficient data transfer. For example, memory storage devices 481 may include a hard disk or other type of mass storage medium that may be enabled to hold large volumes of image, calibration, and scanner parameter data. Scanner 100 may additionally include a barcode reader, RFID detector, Magnetic strip detector, or other type of device that reads one or more identifiers from one or more labels or tags associated with probe array 140. Scanner computer 210 may execute the scan operations based, at least in part, upon one or more data files associated with the identifiers, and store the acquired image data on the hard disk. Additionally, scanner 100 may provide a network file system or FTP service enabling one or more remote computers to query and upload scanned images as well as providing an interface enabling the computer to query scanner data and statistics.

It will be understood by those of ordinary skill in the related art that the operations of scanner computer 210 may be performed by a variety of other servers or computers, such as for instance computer 150, a server such as a GCOS server, or that computer 210 may not necessarily reside in scanner 100.

Cartridge Transport frame 205: Another element of scanner 100 includes cartridge transport frame 205 that provides all of the degrees of freedom required to manipulate probe array 140 for the purposes of auto-focus, scanning, and calibration operations. Those of ordinary skill in the related art will appreciate that the term "degrees of freedom" generally refers to the number of independent parameters required to specify the position and orientation of an object. For example, in one embodiment, probe array 140 may be surrounded or encased by a housing that for instance could include a cartridge with a clear window for optical access to probe array 140. In the present example the cartridge could include one or more features such as a tab or keyed element that interfaces with transport frame 205 and defines the positional relationship of frame 205 and the cartridge. Frame 205 may then manipulate the position of the cartridge relative to one or more elements of scanner 100 such as, for instance, objective lens 345.

In one embodiment, transport frame 205 is capable of manipulating the cartridge in four of six possible degrees of freedom such as, for example, what may be generally referred to as roll, pitch, Z and Y. In the present example, it generally may not be necessary to manipulate a cartridge in the yaw or X axes, but may be possible in some alternative embodiments.

Probe array 140 may be brought into best focus by adjusting the distance of probe array 140 from objective lens 345. In some implementations, the distance adjustment may be employed by moving the position of one or more elements of transport frame 205, such as a focus stage, in the Z axis For example, movement of the focus stage in the Z axis may be actuated by one or more motors in a first direction that may decrease the distance between probe array 140 and objective lens 345, as well as the opposite direction that may increase the distance.

Translation of probe array 140 along the Y-axis may in one embodiment be accomplished by a precision linear stage, coupled to what is referred to as a micro-stepped motor/driver, open loop drive mechanism or other type of motorized mechanism. The linear stage may include a guide element to support and guide the housing or cartridge and additional elements to secure the housing or cartridge during scanner operation. In some embodiments, the linear stage may include independent position adjustment mechanisms enabled to adjust the position of probe array 140 in a plurality of axes such that adjustment in one axis is less likely to affect the adjustments in other axes.

In some implementations, the housing or cartridge generally remains in the same plane of orientation with respect to scanner 100 from the point that it is loaded into scanner 100 to the point at which it is ejected. This may apply to all operations of the scanner including the auto-focus and scan operations. For example, the cartridge may be received by the scanner at the load position in a vertical orientation, where probe array 140 would be located on one of the side faces of the cartridge. While remaining in the same vertical orientation the cartridge is placed into transport frame 205. Probe array 140, housed in the cartridge, is positioned into the best plane of focus by manipulating the cartridge via the pitch, roll, and Z mechanisms. The probe array is then scanned in the X axis by translation of lens 345 as well as the Y axis by translation of transport frame 205. After the completion of the scan operations the cartridge is returned to the load position via transport frame 205 in the same vertical orientation that it was received in.

Additional examples of cartridge transport frames and means for manipulating the position of a probe array for the purposes of scanning are described in U.S. patent application Ser. No. 10/389,194, incorporated by reference above.

Figure 3:
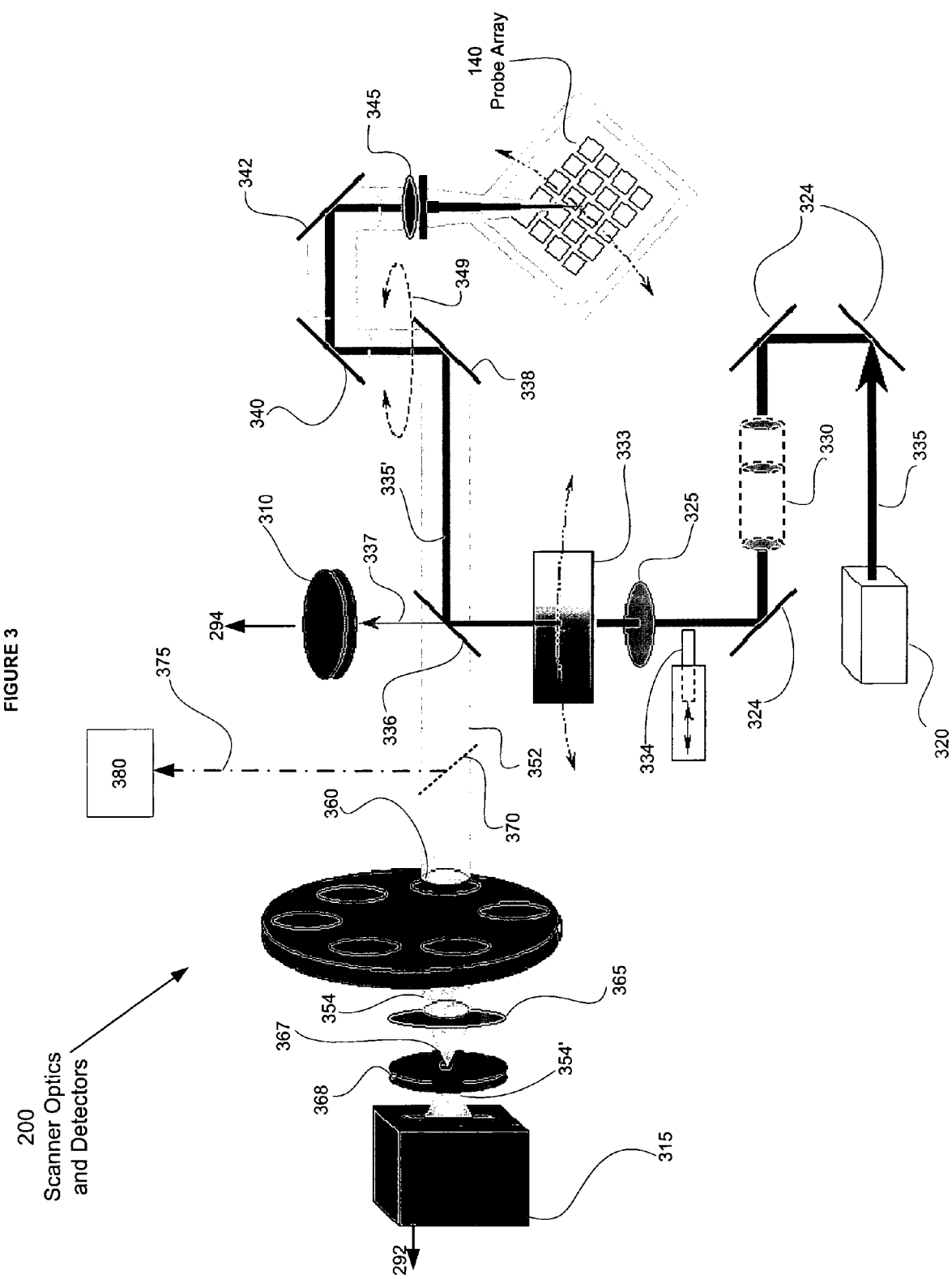
FIG. 3 is a simplified graphical representation of the scanner optics and detectors of FIG. 2, suitable for providing excitation light and the detection of emission signals.

Scanner Optics and Detectors 200: FIG. 3 provides a simplified graphical example of possible embodiments of optical elements associated with scanner 100, illustrated as scanner optics and detectors 200. For example, an element of the presently described invention includes source 320 that could include a laser such as, for instance, a solid state, diode pumped, frequency doubled Nd: YAG (Neodymium-doped Yttrium Aluminum Garnet) or YVO4 laser producing green laser light, having a wavelength of 532 nm or other laser implementation. In the present example, source 320 provides light within the excitation range of one or more fluorescent labels associated with target molecules hybridized to probes disposed on probe array 140 or fluorescent labels associated with a calibration standard. Also in the present example, the wavelength of the excitation light provided by source 320 may be tunable such to enable the use multiple color assays (i.e. employing multiple fluorescent labels with distinct ranges of excitation and emission wavelengths) associated with an embodiment of probe array 103 (Further examples of tunable sources are described in U.S. patent application Ser. No. 10/846,261, titled "System, Method, and Product for Providing a Wavelength-Tunable Excitation Beam", filed May 13, 2004, which is hereby incorporated by reference herein in its entirety for all purposes). Those of ordinary skill in the related art will appreciate that other types of sources 320 may be employed in the present invention such as incandescent sources, one or more light emitting diodes (sometimes referred to as LED's), halogen or xenon sources, metal halide sources, mercury vapor sources, or other sources known in the art. For instance, some embodiments of LED's provide sufficient levels of excitation light to evoke fluorescent emissions from fluorophores, where a single LED may be employed as source 320. LED's of this type provide advantages in certain embodiments over other types of sources due to their low cost, high output efficiency, long life, short on/off—off/on transition time, large selection of wavelengths, and low heat production.

In some embodiments, a single implementation of source 320 is employed that produces a single excitation beam, illustrated in FIG. 3 as excitation beam 335. Alternative embodiments may include multiple implementations of source 320 that each provide excitation light that may be combined into a single beam or directed along separate optical paths to a target, although those of ordinary skill in the related art will appreciate that there are several advantages to implementing a single source over multiple sources such as complexity, space, power, and expense.

Further references herein to source 320 generally will assume for illustrative purposes that they are lasers, but, as noted above, other types of sources, e.g., x-ray sources, light emitting diodes, incandescent sources, metal halide sources, or other electromagnetic sources may be used in various implementations. The Handbook of Biological Confocal Microscopy (James B. Pawley, ed.) (2.ed.; 1995; Plenum Press, NY), includes information known to those of ordinary skill in the art regarding the use of lasers and associated optics, is hereby incorporated herein by reference in its entirety.

FIG. 3 further provides an illustrative example of the paths of excitation beam 335 and emission beam 352 and a plurality of optical components that comprise scanner optics 200. In the present example, excitation beam 335 is emitted from source 320 and is directed along an optical path by one or more turning mirrors 324 toward a three-lens beam conditioner/expander 330. Turning mirrors are commonly associated with optical systems to provide the necessary adjustments to what may be referred to as the optical path such as, for instance, to allow for alignment of excitation beam 335 at objective lens 345 and to allow for alignment of emission beam 354 at detector 315. For example, turning mirrors 324 also serve to "fold" the optical path into a more compact size & shape to facilitate overall scanner packaging. The number of turning mirrors 324 may vary in different embodiments and may depend on the requirements of the optical path. In some embodiments it may be desirable that excitation beam 335 has a known diameter. Beam conditioner/expander 330 may provide one or more optical elements that adjust a beam diameter to a value that could, for instance, include a diameter of 1.076 mm±10%. For example, the one or more optical elements could include a three-lens beam expander that may increase the diameter of excitation beam 335 to a desired value. Alternatively, the one or more optical elements may reduce the diameter of excitation beam 335 to a desired value. Additionally, the one or more optical elements of beam conditioner/expander 330 may further condition one or more properties of excitation beam 335 to provide other desirable characteristics, such as providing what those of ordinary skill in the related art refer to as a plane wavefront to objective lens 345. Excitation beam 335 with the desirable characteristics may then exit beam conditioner/expander 330 and continue along the optical path that may again be redirected by one or more turning mirrors 324 towards excitation filter 325.

Filter 325 may be used to remove or block light at wavelengths other than excitation wavelengths, and generally need not be included if, for example, source 320 does not produce light at these extraneous wavelengths. However, it may be desirable in some applications to use inexpensive sources and often it is cheaper to filter out-of-mode light than to design the source to avoid producing such extraneous emissions. In some embodiments, filter 325 allows all or a substantial portion of light at one or more excitation wavelengths to pass through without affecting other characteristics of excitation beam 335, such as the desirable characteristics modified by beam conditioner/expander 330. Also, a plurality of filters 325 may also be associated with a filter wheel or other means for selectively translating a desired filter in the optical path.

After exiting filter 325 excitation beam 335 may then be directed along the optical path to laser attenuator 333. Laser attenuator 333 may provide a means for adjusting the level of power of excitation beam 335. In some embodiments, attenuator 333 may, for instance, be comprised of a variable neutral density filter. Those of ordinary skill in the related art will appreciate that neutral density filters, such as absorptive, metallic, or other type of neutral density filter, may be used for reducing the amount of light that is allowed to pass through. The amount of light reduction may depend upon what is referred to as the density of the filter, for instance, as the density increases the amount of light allowed to pass through decreases. The neutral density filter may additionally include a density gradient. For example, the presently described embodiment may include laser attenuator 333 that includes a neutral density filter with a density gradient. Attenuator 333, acting under the control of applications 272 and/or firmware 472 may use a step motor that alters the position of the neutral density filter with respect to the optical path. The neutral density filter thus reduces the amount of light allowed to pass through based, at least in part, upon the position of the filter gradient relative to the optical path. In the present example, the power level of excitation beam is measured by laser power monitor 310 that is described further below, and may be dynamically adjusted to a desired level.

Some embodiments may include one or more implementations of shutter 334. Some implementations may include positioning shutter 334 in one or more locations within scanner 100, along the optical path such that shutter 334 provides a means to block all excitation light from reaching probe array 140, and in some implementations additionally blocking all excitation light from reaching laser power monitor 310. Shutter 334 may use a variety of means to completely block excitation beam 335. For example shutter 334 may use a motor under the control of applications 272 and/or firmware 472 to extend/retract a solid barrier that could be constructed of metal, plastic, or other appropriate material capable of blocking essentially all light from source 320, such as excitation beam 335. Shutter 334 may be used for a variety of purposes such as, for example, for blocking all light from one or more photo detectors or monitors, including detector 315 and power monitor 310. In the present example, blocking the light may be used for calibration methods that measure and make adjustments to what is referred to as the "dark current" or background noise generated from a number of possible sources such as one or more of the photo detectors, electrical interference, or other sources of noise known to those of ordinary skill in the related art.

Components of scanner optics and detectors 200 placed in the optical path after elements such as attenuator 333 and/or shutter 334 may include dichroic beam splitter 336. Those of ordinary skill in the related art will appreciate that a dichroic beam splitter, also commonly referred to as a dichroic mirror, may include an optical element that is highly reflective to light of a certain wavelength range, and allow transmission of light through the beam splitter or mirror at one or more other wavelength ranges. In some embodiments, beam splitter 336 could also include what is referred to as a geometric beam splitter where a portion of the surface of beam splitter 336 is reflective to all light or light within a particular range of wavelengths, and the remaining portion is permissive to the light. Also, some embodiments of dichroic beam splitter 336 may reflect a certain percentage of light at a particular wavelength and allow transmission of the remaining percentage. For example, dichroic beam splitter 336 may direct most of the excitation beam, illustrated as excitation beam 335', along an optical path towards objective lens 345 while allowing the small fractional portion of excitation beam 335 that is not reflected to pass through beam splitter 336, illustrated in FIG. 3 as partial excitation beam 337. In the present example, partial excitation beam 337 passes through dichroic beam splitter 336 to laser power monitor 310 for the purpose of measuring the power level of excitation beam 335 and providing feedback to applications 272 and/or firmware 472. Applications 272 and/or firmware 472 may then make adjustments, if necessary, to the power level via laser attenuator 333 as described above.

Monitor 310 may be any of a variety of conventional devices for detecting partial excitation beam 337, such as a silicon detector for providing an electrical signal representative of detected light, a photodiode, a charge-coupled device, a photomultiplier tube, or any other detection device for providing a signal indicative of detected light that is now available or that may be developed in the future. As illustrated in FIG. 3, detector 310 generates excitation signal 294 that represents the detected signal from partial excitation beam 337. In accordance with known techniques, the amplitude, phase, or other characteristic of excitation signal 294 is designed to vary in a known or determinable fashion depending on the power of excitation beam 335. The term "power" in this context refers to the capability of beam 335 to evoke emissions. For example, the power of beam 335 generally refers to photon number or energy per unit of time and typically may be measured in milliwatts of laser energy with respect to the illustrated example in which the laser energy evokes a fluorescent signal. Thus, excitation signal 294 includes values that represent the power of beam 335 during particular times or time periods. Applications 272 and/or firmware 472 may receive signal 294 for evaluation and, as described above, if necessary make adjustments.

After reflection from beam splitter 336, excitation beam 335' may continue along an optical path that may in some embodiments be directed via periscope mirror 338, turning mirror 340, and arm end turning mirror 342 to objective lens 345. In the illustrated implementation mirrors 338, 340, and 342 may have the same reflective properties as turning mirrors 324, and could, in some implementations, be used interchangeably with turning mirrors 324.

Lens 345 in the illustrated implementation may include a small, light-weight lens located on the end of an arm that is driven by a galvanometer around an axis perpendicular to the plane represented by galvo rotation 349. In one embodiment, lens 345 focuses excitation beam 335' down to a specified spot size at the best plane of focus that could, for instance, include a 3.5 µm spot size. Galvo rotation 349 results in objective lens 345 moving in an arc over a substrate, providing what may be referred to as an arcuate path that may also be referred to herein as a "scanning line", upon which biological materials typically have been synthesized or have been deposited. The arcuate path may, for instance, move in a 36 degree arc over a substrate. One or more fluorophores associated with the biological materials emit emission beam 352 at characteristic wavelengths in accordance with well-known principles. The term "fluorophore" commonly refers to a molecule which will absorb energy of a specific wavelength and re-emit energy at a different wavelength. For example, excitation beam 335' may be focused to a spot by objective lens 345 and translated in a particular axis with respect to probe array 140 thus providing excitation energy to the probe features along that axis. Additional means of translation may also include a voice coil, rotating mirror, or other means known to those of ordinary skill in the related art.

Emission beam 352 in the illustrated example follows the reverse optical path as described with respect to excitation beam 335' until reaching dichroic beam splitter 336. In accordance with well known techniques and principles, the characteristics of beam splitter 336 are selected so that beam 352 (or a portion of it) passes through the mirror rather than being reflected. Emission beam 352 is then directed along a desired optical path to filter wheel 360.

In one embodiment, filter wheel 360 may be provided to filter out spectral components of emission beam 352 that are outside of the emission spectra of one or more particular fluorophores. The term "emission spectra" generally refers to one or more characteristic emission wavelengths or range of wavelengths of those fluorophores that are responsive to excitation beam 335. In some implementations filter wheel 360 is capable of holding a plurality of filters that each could be tuned to different wavelengths corresponding to the emission spectra from different fluorophores. Filter wheel 360 may include a mechanism for turning the wheel to position a desired filter in the optical path of emission beam 352. The mechanism may include a motor or some other device for turning or translation that may be responsive to instructions from application 272 and/or firmware 472. For example, excitation beam 335 from source 320 may comprise one or more wavelengths that may include a range of wavelengths that excite one or more fluorophore species where the amount of energy absorbed and re-emitted by each fluorophore species in its emission spectra is a function of its extinction coefficient and the power level of beam 335. In the present example, filter wheel 360 may be translated with respect to the optical path of emission beam 352 to position a filter that is complementary to the emission spectra of the particular fluorophore species in order to remove light components from emission beam 352 that are outside of the emission spectra. The source of the undesirable light components could include undesirable fluorescence generated by other fluorophore species, emissions from glass, glue, or other components associated with housings for probe array 140, or other sources known to those of ordinary skill in the related art.

As an additional example, biological probe array experiments could be carried out on the same implementation of probe array 140 where a plurality of fluorophore species each with different emission spectra are used that could be excited by a single source. In the present example, multiple fluorescent species could be used that have the same excitation wavelengths but have differing emission spectral properties could be produced by methods such as those known to those in the art as fluorescent resonant energy transfer (FRET), or semiconductor nanocrystals (sometimes referred to as Quantum Dots), which are discussed in greater detail below with respect to system gain adjustment. Those of ordinary skill in the related art will appreciate that FRET may be achieved when there are two fluorophore species present in the same molecule. The emission wavelength of one fluorophore overlaps the excitation wavelength of the second fluorophore and results in the emission of a wavelength from the second fluorophore that is atypical of the class of fluorophores that use that excitation wavelength. Also, quantum dots are tunable such that multiple quantum dot species may be employed that each specie excites at a particular wavelength but has a different characteristic emission spectra. Thus by using an excitation beam of a single wavelength it is possible to obtain distinctly different emissions so that different features of a probe array could be labeled in a single experiment. In the present example, filter wheel may include a complementary filter for each fluorophore species associated with probe array 140. The result may include filtered emission beam 354 that is a representation of emission beam 352 that has been filtered by a desired filter of filter wheel 360.

In other implementations, multiple excitation sources 320 (or one or more adjustable-wavelength excitation sources) and corresponding multiple optical elements in optical paths similar to the illustrated one could be employed for simultaneous scans at multiple wavelengths. Other examples of scanner systems that utilize multiple emission wavelengths are described in U.S. Pat. No. 6,490,533, titled "System, Method, and Product For Dynamic Noise Reduction in Scanning of Biological Materials", filed Dec. 3, 2001; U.S. Pat. No. 6,650,411, titled "System, Method, and Product for Pixel Clocking in Scanning of Biological Materials", filed Dec. 3, 2001; and U.S. Pat. No. 6,643,015, titled "System, Method, and Product for Symmetrical Filtering in Scanning of Biological Materials", filed Dec. 3, 2001 each of which are hereby incorporated by reference in their entireties for all purposes.

In accordance with techniques well known to those of ordinary skill in the relevant arts, including that of confocal microscopy, beam 354 may be focused by various optical elements such as lens 365 and passed through illustrative pinhole 367, aperture, or other element. In accordance with known techniques, pinhole 367 is defined by and comprises an opening or aperture in substrate 368 and is positioned such that it rejects light from focal planes other than the plane of focus of objective lens 345 (i.e., out-of-focus light), and thus increases the resolution of resulting images.

In some implementations, pinhole 367 may be bi-directionally moveable along the optical path. As those of ordinary skill in the related art will appreciate, the appropriate placement of pinhole 367 to reject out of focus light is dependant upon the emission spectra of beam 354 and the diameter of pinhole 367. Those of ordinary skill in the related art will appreciate that it is desirable in many embodiments to reduce the diameter of pinhole 367 to a minimum size associated with the desired focal plane in order to reduce the level of "background" noise in the detected signal. Pinhole 367 may be movable via a motor or other means under the control of applications 272 and/or firmware 472 to a position that corresponds to the emission spectra of the fluorophore species being scanned. In the same or alternative embodiments, pinhole 367 may comprise a sufficiently large diameter to accommodate the wavelengths in the emission spectra of several fluorophore species if those wavelengths are relatively similar to each other, although as described above increasing the diameter of the pinhole may have negative consequences. Also, some embodiments of pinhole 367 may include an "iris" type of aperture that expands and contracts so that the diameter of the hole or aperture is sufficient to permit the desired wavelength of light at the plane of focus to pass through while rejecting light that is substantially out of focus.

Alternatively, some embodiments may include a series of pinholes 367. For example, there may be an implementation of pinhole 367 associated with each fluorophore species associated with probe array 140. Each implementation of pinhole 367 may be placed in the appropriate position to reject out of focus light corresponding to the emission spectra of its associated fluorophore. Each of pinholes 367 may be mounted on a translatable stage, rotatable axis, or other means to move pinhole 367 in and out of the optical path. In the present example, the implementation of pinhole 367 corresponding to the fluorophore species being scanned is positioned in the optical path under the control of applications 272 or firmware 472, while the other implementations of pinhole 367 are positioned outside of the optical path thus allowing the implementation of pinhole 367 in the optical path to reject out of focus light.

After passing through pinhole 367, the portion of filtered emission beam 354 that corresponds to the plane of focus, represented as filtered emission beam 354', continues along a desired optical path and impinges upon detector 315.

Similar to excitation detector 310, emission detector 315 may be a silicon detector for providing an electrical signal representative of detected light, or it may be a photodiode, a charge-coupled device, a photomultiplier tube, or any other detection device that is now available or that may be developed in the future for providing a signal indicative of detected light. Detector 315 generates signal 292, that may in some embodiments comprise values associated with photon counts or other measure of intensity that represents filtered emission beam 354' in the manner noted above with respect to the generation of excitation signal 294 by detector 310. Signal 292 and excitation signal 294 may be provided to applications 272 and/or firmware 472 for processing, as previously described.

Color Correcting Lens 365': As described above, some embodiments of scanner 100 may be enabled for the detection of multiple wavelengths of emitted light in response to providing excitation light of a single wavelength generated by a single implementation of source 320. For example, some assays designed for use with implementations of probe array 140 may include multiple fluorophore species used as labels each employed to distinguish different elements, such as for instance what are referred to as genotyping assays where each of the fluorescent species may be associated with a particular nucleic acid. In the present example, there may be four different emission spectra each corresponding to a label that is associated with one of four nucleic acid species that enables the unambiguous identification of the presence of nucleic acid composition in a sequence.

Those of ordinary skill in the related art will appreciate that each emission spectra may comprise a peak wavelength that comprises the wavelength with the highest transmission efficiency for the spectra therefore providing the highest percent emission intensity for the input power of excitation light. Also, optical components typically demonstrate wave-length dependent properties such as for instance what may be referred to as chromatic aberration associated with the index of refraction of each wavelength as it passes through lens elements. The term "chromatic aberration" generally refers to a wavelength dependent difference in focal length of a lens, where for example blue light (includes a range of short wavelengths) will focus at a different point than red light (includes a range of long wavelengths) when passing through the same lens. An example, of chromatic aberration is presented in FIG. 5A that illustrates 3 different wavelengths 510, 520, and 530, each having a different focal point that is based upon the focal length and chromatic aberration associated with lens 365 that focuses light at pinhole 367. In the present example focal point 535 is associated with wavelength 530 and focuses substantially in front of pinhole 367, focal point 550 is associated with wavelength 520 and focuses at the plane of pinhole 367, and the focal point associated with wavelength 510 (Not shown) focuses substantially past pinhole 367.

Figure 5A:
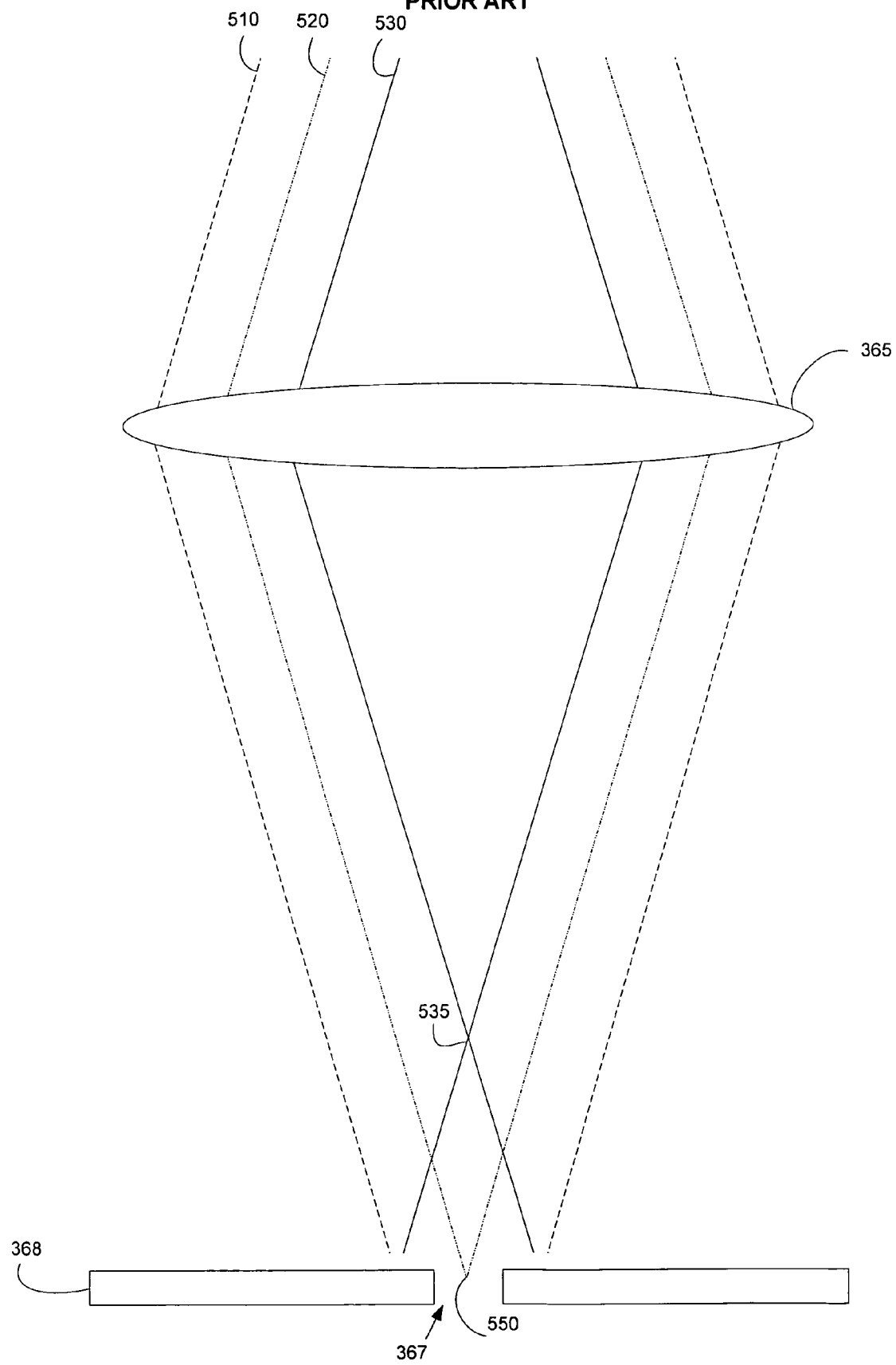
FIG. 5A is a simplified graphical illustration of one embodiment of a standard lens associated with the optics and detectors of FIG. 3 for focusing light at a pinhole.

Also, the example of FIG. 5A illustrates the beams that comprise each of wavelengths 510, 520 and 530 as each having a different diameter when they impinge upon lens 365 that could for instance include effects of chromatic aberration effects associated with objective lens 345. In the present example, the effects of focal length difference with respect to wavelengths 510, 520, and 530 may also include what may be referred to as spherical aberration effects where the index of refraction is different near the edge of a spherical lens than it is in comparison to the center of the lens where the effects are independent of wavelength.

Figure 5B:
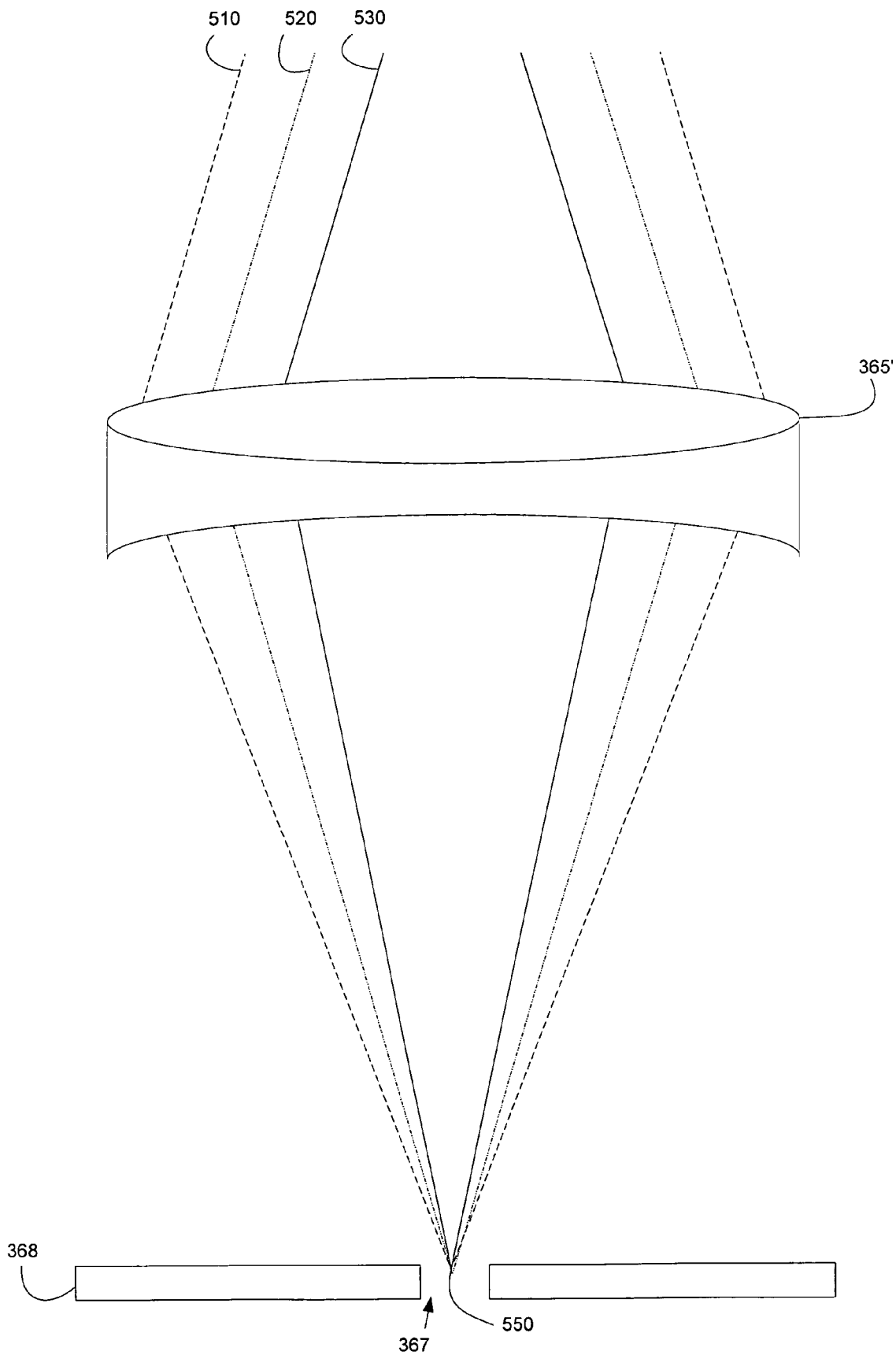
FIG. 5B is a simplified graphical illustration of one embodiment of a color correcting lens associated with the optics and detectors of FIG. 3 that corrects for wavelength and spatial dependent differences in focal length and focuses multiple wavelengths at a pinhole.

FIG. 5B illustrates color correcting lens 365' where both the chromatic and spherical aberration effects associated with each of wavelengths 510, 520, and 530 is corrected to have the same focal point 650 where focal point 650 is substantially at the same plane parallel to the axis of substrate 368 that defines pinhole 367. Those of ordinary skill in the related art will appreciate that color correcting lens 365' is not the same as what is generally referred to as a true achromatic lens enabled to compensate for chromatic aberration because lens 365' corrects for both chromatic and spherical aberration effects. For example, achromatic lenses generally may be employed near the beginning of the optical path and may for instance be an implementation of objective lens 345 that "achromatizes" the entire system. A drawback to such an implementation is that achromatic lenses are typically large multi-element lenses that comprise a comparatively large mass as opposed to a preferred implementation of objective lens 345 that is low mass and useful for rapid translation at a consistent velocity across what may be referred to the "fast" axis employed for acquisition of a line of pixel data.

Embodiments of lens 365' may be located substantially at the end of the optical path that focuses multiple wavelengths of light of emission beam 354 at pinhole 367 where lens 365' may correct for the wavelength dependent differences as well as spatial dependent differences in the index of refraction employing one or more sets of multiple lens elements. Each lens element may have a different index of refraction effect on each of the wavelengths and associated wavelength-dependent diameter with the result of each wavelength having the same focal length as it leaves the last lens element. Therefore, lens 365' compensates for the combination of spatial and wavelength dependent characteristics associated with each wavelength so that the focal length for each wavelength is the same. In the present example, four wavelengths may be employed where each wavelength is known and distinct and can be corrected for by lens 365'.

Figure 5C:
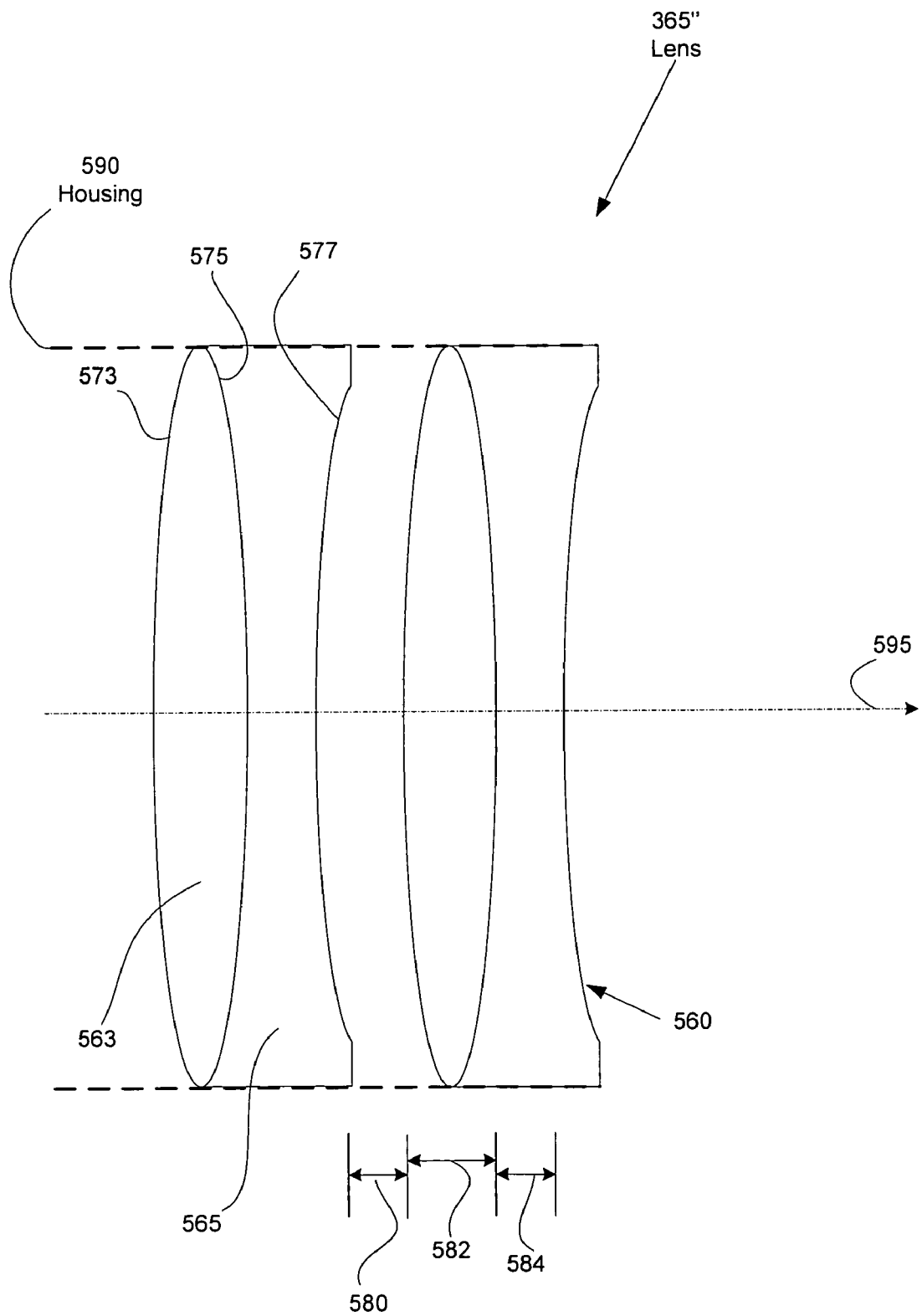
FIG. 5C is a simplified graphical illustration of a second embodiment of a color correcting lens associated with the optics and detectors of FIG. 3 that corrects for wavelength dependent differences in focal length.

FIG. 5C provides an illustrative example of a multiple lens embodiment for color correction as lens 365". Lens 365" may comprise elements such as housing 590 that may protect against foreign objects as well as blocking undesirable light, and multiple lens components 560 each comprising one or more lens elements such as element 563 and 565. In the illustrated example, each lens component 560 of lens 365" may be identical each comprising the same elements and in cooperation provide the same function as described above with respect to lens 365'.

Each lens component 560 may comprise a plurality of lens elements such as for example elements 563 and 563 that each provide specific optical characteristics that may be defined by one or more parameters. The parameters may include glass composition, where specific glass types may have particular desirable indicies of refraction, and in particular have desirable indicies of refraction with respect to the multiple wavelengths employed in a probe array assay. For example, in some embodiments element 563 may be composed of what may be referred to as N—SK5 Optical Glass and element 565 may be composed of N—SF57 Optical Glass.

In addition, other factors such as radius and thickness characteristics of each element affect the optical properties. For example, element 563 may include radius 573 that could in some implementations include a leading edge (i.e. side that light enters the lens) radius of 14.841 mm±0.05 mm with a chromatic aperture of 14.3 mm; and a trailing edge (i.e. side that light exits the lens) radius 575 that could in some implementations include a radius of −23.629 mm±0.05 mm with a chromatic aperture of 13.5 mm. Also in the present example, element 565 may comprise a complementary radius to radius 575 so that both elements 563 and 565 operatively couple without spaces or gaps between elements. Element 565 may also include radius 577 that could in some implementations include a trailing edge radius of 30.500 mm±0.05 mm and a chromatic aperture of 12.5 mm. In the presently described example each of the radii may be measured from center line 595. Continuing the example from above, each of elements 563 and 565 may include dimensions such as thickness characteristics (measured at the apex of the aforementioned radii) that also affect their optical properties, for instance element 563 may include a thickness of 5.4725 mm±0.1 mm and element 565 may include a thickness of 2.0 mm±0.1 mm. Further, lens 365" may include a diameter of 16.0 mm±0.25 mm. In addition the spacing between implementations of component 560 (illustrated as spacing 580) may also be important, and for instance spacing 580 may include a distance of 1 mn.

System Gain Adjustment: In some embodiments, it may be advantageous to adjust one or more gain elements of scanner 100 that may in some embodiments include setting the power of excitation beam 335 that is delivered to probe array 140 to a preferred power level that provides an optimal signal to noise ratio (i.e. highest emission signal to lowest background noise) response from a particular fluorophore species. For example, some assays may employ fluorescent labels such as what may be referred to as semiconductor nanocrystals (sometimes referred to as Quantum Dots). Those of ordinary skill in the related art will appreciate that semiconductor nanocrystals include manufactured elements that fluoresce in response to a range of excitation wavelengths. Semiconductor nanocrystals have a number of useful characteristics including a high degree of resistance to what may be referred to as photobleaching, and the ability of manufacturers to tune the excitation and emission spectra of each semiconductor nanocrystal based upon certain characteristics such as the size of the element. In the present example, each semiconductor nanocrystal specie has a characteristic absorption spectrum over which photons of light are absorbed at a rate that is dependent upon what may be referred to as the extinction coefficient for a given excitation wavelength for that embodiment of semiconductor nanocrystal. In the present example, it may be desirable to provide a preferred level of power of excitation beam 335 at the given excitation wavelength, which in the present example may include a wavelength of 532 nm, that substantially saturates the fluorophore/semiconductor nanocrystal specie in order to maximize the level of fluorescent emission without substantially exceeding the preferred level of power. When the preferred level of power is exceeded the signal from the fluorophore species at the plane of focus are saturated and do not provide additional emission signal, but undesirable emission signal from fluorophore species from outside the plane of focus may be encountered due to excitation from the excess power that promotes the addition of background noise and thus quickly deteriorates the optimal signal to noise ratio. In some instances, the undesirable emissions could increase at a rate that is substantially linear to the excess input power. Those of ordinary skill in the related art will appreciate that since each fluorophore/semiconductor nanocrystal species may include a characteristic extinction coefficient at the given excitation wavelength, each such embodiment also includes a preferred power level for excitation beam 335 to achieve saturation. In addition, those of ordinary skill in the related art will appreciate that the example described above should not be limited to semiconductor nanocrystals and that other fluorophore species may also be used as previously described.

Figure 6:
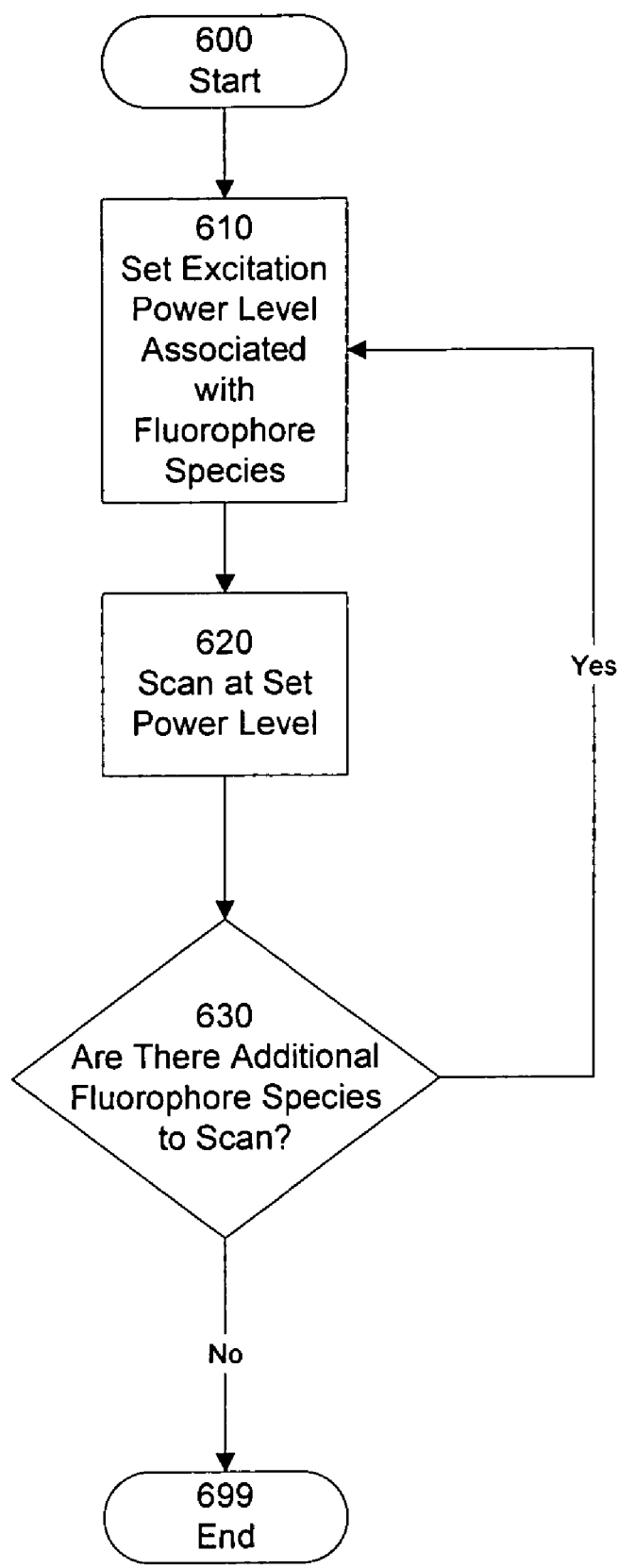
FIG. 6 is a functional block diagram of a method of adjusting system gain that includes setting the optimal power of an excitation beam provided by the optics and detectors of FIG. 3 that maximizes the signal to noise ratio associated with a fluorophore species.

Some embodiments of the present invention include adjusting the power of excitation beam 335 for each fluorophore specie in an assay so that the detected emissions are maximized and comparable to one another. FIG. 6 illustrates an exemplary method of gain adjustment that includes step 610 of setting the excitation power of excitation beam 335 to an optimal power level for an associated fluorophore specie to be scanned. As previously described, data such as the excitation power levels other data associated with each fluorophore specie may be encoded in machine readable form such as a barcode, RFID tag, magnetic strip, etc affixed to the substrate of probe array 140 or to an associated cartridge or housing of probe array 140; and/or be used as or associated with one or more identifiers and stored in experiment data 277, library files 274, and/or scanner parameter data 477. The power level or other data may be accessed and implemented by instrument control and image analysis applications 272 and/or scanner firmware 472 or any combination thereof. The power level of beam 335 may be adjusted by controlling input power to source 320, attenuated by laser attenuator 335, or by other means known in the art.

Step 620 illustrates the step of scanning and collecting the detected emissions from the desired fluorophore specie that includes signal 292. Various methods of scanning exist in various embodiments where in one embodiment the entire area of probe array 140 may be scanned using the set power level, alternatively it may be advantageous in some embodiments to scan line by line, or even further some embodiments may include adjusting the power and scanning pixel by pixel or by sets of two or more pixels, or other sub-area of probe array 140. Step 630 includes a decision element of whether the assay includes additional fluorophore to scan in the unit of area to be scanned (i.e. line, pixel, etc.). If there are the method returns to step 610 and set the power of beam 335 for the next fluorophore.

For example, four species of semiconductor nanocrystals may be employed in an assay with probe array 140 that each is excited by a wavelength of 532 nm. Applications 272 or firmware 472 could translate the appropriate filter into the optical path and set the excitation power to a pre-determined level for the first species, such as for instance a level of 0.3 mW for the first species that emits a wavelength of 705 nm and initiate a scan of probe array 140 as previously described, collecting the resulting emission intensity data. Similarly, Applications 272 or firmware 472 iterates through the remaining species that may for instance include a power level of 2 mW for a second species that emits a wavelength of 655 nm; a power level of 3 mW for a second species that emits a wavelength of 605 nm; and a power level of 6 mW for a second species that emits a wavelength of 565 nm. The result could include four sets of data, one for each species that could include an image for each set of data that could subsequently be combined into a single image representative of all data acquired from probe array 140.

Those of ordinary skill in the related art will appreciate that using the same wavelength of excitation light may excite each fluorophore specie in the associated assay and consequently produce emissions of non-selected wavelengths that could introduce noise and confound the analysis of the emission data from the selected fluorophore. Embodiments of the present invention include specific filters in filter wheel 360 that are permissive to a selected wavelength or range of wavelengths and non-permissive to all others. Additionally, for some fluorophore species with differing extinction coefficients for a given excitation wavelength only the fluorophore specie excited at the preferred power level will deliver the optimal emission intensity and all other species will produce lower intensity levels. For example, filter wheel 360 may position a first filter in the optical path that correspond to a first emission wavelength, where only the first wavelength corresponding with the emissions of a fluorophore specie in the associated assay passes through to detector 315, and the emissions that correspond to the other fluorophores are rejected. In the present example, when the excitation power level is set at step 610, the appropriate filter may be positioned in the optical path by applications 272 or firmware 472. Also, filter data, filter position in filter wheel 360, and other filter related information may be stored and retrieved from experiment data 277, library files 274, and/or scanner parameter data 477.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A method for detecting a plurality of fluorophore species on a biological probe array using a single excitation source scanner, comprising:
   (a) providing an biological probe array comprising at least two fluorophores, wherein said at least two fluorophores are semiconductor nanocrystals and each has a different extinction coefficient,
   (b) providing a scanner comprising a single excitation beam source;
   (c) setting the excitation beam comprising an excitation wavelength at a first power level that elicits an optimal signal to noise ratio response from a first fluorophore having a first extinction coefficient;
   (d) scanning the biological probe array with the excitation beam at the first power level, thereby eliciting a light emission at a first wavelength from the first fluorophore;
   (e) detecting the first emission wavelength emitted from the biological probe array;
   (f) setting the excitation beam comprising the excitation wavelength at a second power level different than the first power level, wherein the second power level elicits an optimal signal to noise ratio response from a second fluorophore; and
   (g) scanning the biological probe array with the excitation beam at the second power level, thereby eliciting a light emission at a second wavelength from the second fluorophore which is at a different wavelength from the first emission wavelength;
   (h) detecting the second emission wavelength emitted from the biological probe array;
   thereby detecting a plurality of fluorophores on the biological probe array.

2. The method of claim 1, further comprising:
   setting the excitation beam comprising the excitation wavelength at a third power level different than the first and second power levels, wherein said third power level setting elicits an optimal signal to noise ratio response from a third fluorophore;
   scanning the biological probe array with the excitation beam at the third power level, thereby eliciting a third emission wavelength from the third fluorophore, which is at a different wavelength than the first and second emission wavelengths;
   setting the excitation beam comprising the excitation wavelength at a fourth power level different than the first, second, and third power levels, wherein said fourth power level setting elicits an optimal signal to noise ratio response from a fourth fluorophore; and
   scanning the biological probe array with the excitation beam at the fourth power level, thereby eliciting a fourth emission wavelength from the fourth fluorophore, which is at a different wavelength than the first, second and third emission wavelengths.

3. The method of claim 2, wherein: the first, second, third, and fourth power levels comprise 0.3 mW, 2 mW, 3 mW, and 6 mW respectively.

4. The method of claim 2, wherein the first, second, third, and fourth fluorophores emit light at characteristic wavelengths of 705 nm, 655 nm, 605 nm, and 565 nm respectively.

5. The method of claim 1, wherein the excitation wavelength is 532 nm.

6. The method of claim 1, wherein the optimal signal to noise ratio comprises a ratio of highest amount of signal from the fluorophore to a lowest level of background noise.

7. The method of claim 1, wherein the first power level substantially excites the first fluorophore without substantially exciting additional fluorophores from outside a plane of focus, and the second power level substantially saturates the second fluorophore without substantially exciting additional fluorophores from outside the plane of focus.

8. The method of claim 1, wherein the first power level is selected based on an extinction coefficient characteristic of the first fluorophore, and the second power level is selected based on an extinction coefficient characteristic of the second fluorophore.

9. The method of claim 1, wherein setting the first and second power levels comprises adjusting an input power to a laser source.

10. The method of claim 1, wherein: setting the first and second power levels comprise attenuating the excitation beam.

11. The method according to claim 1, wherein said method further comprises providing specific wavelength filters in a filter wheel, wherein the wavelength filters are permissive to a selected wavelength or range of wavelengths and non-permissive to all other wavelengths, and wherein said wavelength or range of wavelengths comprise said first and second emission wavelengths.

12. The method according to claim 1, wherein said method further comprises displaying data representing the emissions at the first and second wavelengths on a computer screen in the form of one or more images, thereby allowing an end user to readily visualize and associate the emissions with the at least two fluorophores.

13. A system for scanning a plurality of fluorophores on a biological probe array, comprising:
   an instrument control application stored for execution in system memory of a computer, wherein the application performs the method comprising:
   (a) providing an biological probe array comprising at least two fluorophores, wherein the at least two fluorophores are semiconductor nanocrystals and each has a different extinction coefficient;
   (b) providing a scanner comprising a single excitation beam source;
   (c) setting an excitation beam comprising an excitation wavelength at a first power level that elicits an optimal signal to noise ratio response from a first fluorophore having a first extinction coefficient;
   (d) scanning the biological probe array with the excitation beam at the first power level, thereby eliciting a first emission wavelength from the first fluorophore;
   (e) detecting the first emission wavelength emitted from the biological probe array;
   (f) setting the excitation beam comprising the excitation wavelength at a second power level different than the first power level, wherein the second power level elicits an optimal signal to noise ratio response from a second fluorophore;

(g) scanning the biological probe array with the excitation beam at the second power level, thereby eliciting a second emission wavelength from the second fluorophore which is at a different wavelength from the first emission wavelength; and (h) detecting the second emission wavelength emitted from the biological probe array;

thereby detecting a plurality of fluorophores on the biological probe array.

14. The system of claim 13, wherein the method further comprises:

setting the excitation beam comprising the excitation wavelength at a third power level different than the first and second power levels, wherein said third power level setting elicits an optimal signal to noise ratio response from a third fluorophore;

scanning the biological probe array with the excitation beam at the third power level, thereby eliciting a third emission wavelength from the third fluorophore which is at a different wavelength from the first and second emission wavelengths;

setting the excitation beam comprising the excitation wavelength at a fourth power level different than the first, second, and third power levels, wherein said fourth power level setting elicits the optimal signal to noise ratio response from a fourth fluorophore; and scanning the biological probe array with the excitation beam at the fourth power level, thereby eliciting a fourth emission wavelength from the fourth fluorophore which is at a different wavelength than from the first, second and third emission wavelengths.

15. The system of claim 14, wherein the first, second, third, and fourth power levels are 0.3 mW, 2 mW, 3 mW, and 6 mW, respectively.

16. The system of claim 14, wherein the first, second, third, and fourth fluorophores emit light at the wavelengths of 705 nm, 655 nm, 605 nm, and 565 nm, respectively.

17. The system of claim 13, wherein the excitation wavelength is 532 nm.

18. The system of claim 13, wherein the optimal signal to noise ratio comprises a ratio of highest amount of signal from the fluorophore to a lowest level of background noise.

19. The system of claim 13, wherein the first power level substantially excites the first fluorophore without substantially exciting additional fluorophores from outside a plane of focus, and the second power level substantially saturates the second fluorophore without substantially exciting additional fluorophores from outside the plane of focus.

20. The system of claim 13, wherein the first power level is selected based on an extinction coefficient characteristic of the first fluorophore, and the second power level is selected based on an extinction coefficient characteristic of the second fluorophore.

21. The system of claim 13, wherein setting the first and second power levels comprises adjusting an input power to a laser source.

22. The system of claim 13, wherein setting the first and second power levels comprises attenuating the excitation beam.

23. The system according to claim 13, wherein the system performs said method which further comprises:

providing specific wavelength filters in a filter wheel, wherein said filters are permissive to a selected wavelength or range of wavelengths and non-permissive to all other wavelengths, and wherein said wavelength or range of wavelengths comprise the first and second emission wavelengths.

24. The system according to claim 13, wherein the system performs said method which further comprises:

displaying data representing emissions at the first and second wavelengths on a computer screen in the form of one or more images, thereby allowing an end user to readily visualize and associate the emissions with the at least two fluorophores.

\* \* \* \* \*